US00PP35067P2

(12) United States Plant Patent
Bentley et al.

(10) Patent No.: US PP35,067 P2
(45) Date of Patent: Mar. 21, 2023

(54) ***POLEMONIUM* PLANT NAMED 'GOLDEN FEATHERS'**

(50) Latin Name: *Polemonium pulcherrimum*
Varietal Denomination: 'Golden Feathers'

(71) Applicant: PLANT GROWERS AUSTRALIA PTY. LTD., Wonga Park (AU)

(72) Inventors: Howard Bentley, Wonga Park (AU); Steven Eggleton, Wonga Park (AU)

(73) Assignee: PLANT GROWERS AUSTRALIA PTY. LTD., Wonga Park (AU)

( * ) Notice: Subject to any disclaimer, the term of this patent is extended or adjusted under 35 U.S.C. 154(b) by 0 days.

(21) Appl. No.: 17/903,919

(22) Filed: Sep. 6, 2022

Related U.S. Application Data

(60) Provisional application No. 63/244,947, filed on Sep. 16, 2021.

(51) Int. Cl.
*A01H 5/02* (2018.01)
*A01H 6/70* (2018.01)

(52) U.S. Cl.
USPC ..... Plt./470
CPC ..... *A01H 6/70* (2018.05)

(58) Field of Classification Search
USPC ..... Plt./470
CPC ..... A01H 6/70
See application file for complete search history.

*Primary Examiner* — Anne Marie Grunberg
(74) *Attorney, Agent, or Firm* — C. Anne Whealy

(57) ABSTRACT

A new and distinct cultivar of *Polemonium* plant named 'Golden Feathers', characterized by its upright to somewhat outwardly spreading and mounding plant habit; dense and bushy appearance; green and yellow green variegated leaves; freely flowering habit; light purple-colored flowers; good garden performance; and resistance to Powdery Mildew.

2 Drawing Sheets

Figure 1:
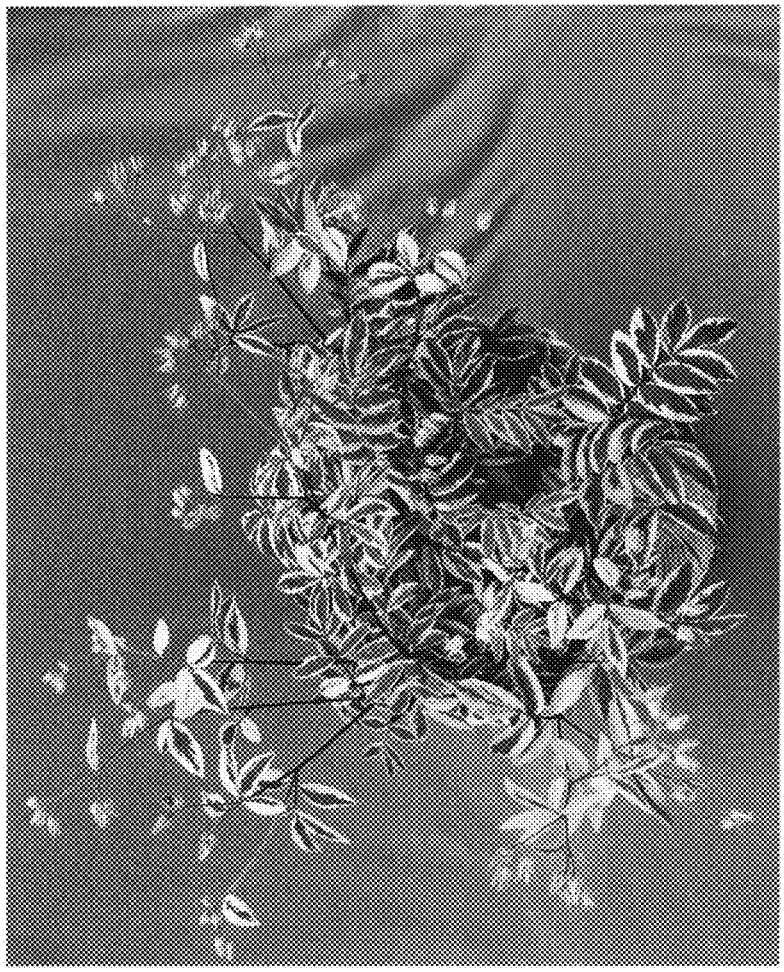

Botanical designation: *Polemonium pulcherrimum.*
Cultivar denomination: 'GOLDEN FEATHERS'.

STATEMENT REGARDING PRIOR DISCLOSURES BY INVENTORS/APPLICANTS

An European Community Plant Breeders' Rights application was filed for the instant plant filed on Dec. 15, 2020, application number 2020/3304. Foreign priority is not claimed to this application.

An United Kingdom Plant Breeders' Rights application was filed for the instant plant filed on Jan. 31, 2022, application number 30/842. Foreign priority is not claimed to this application.

An Australia Plant Breeders' Rights application was filed for the instant plant filed on May 12, 2022, application number 2022/090. Foreign priority is not claimed to this application.

BACKGROUND OF THE INVENTION

The present invention relates to a new and distinct cultivar of *Polemonium* plant, botanically known as *Polemonium pulcherrimum*, commonly known as Jacob's Ladder and hereinafter referred to by the name 'Golden Feathers'.

The new *Polemonium* plant is a naturally-occurring whole plant mutation of *Polemonium pulcherrimum* 'Lambrook Mauve', not patented. The new *Polemonium* plant was discovered and selected by the Inventors as a single plant from within a population of plants of 'Lambrook Mauve' in a controlled greenhouse environment in Wonga Park, Victoria, Australia in October, 2016.

Asexual reproduction of the new *Polemonium* plant by terminal cuttings in a controlled greenhouse environment in Wonga Park, Victoria, Australia since October, 2016 has shown that the unique features of this new *Polemonium* plant are stable and reproduced true to type in successive generations.

SUMMARY OF THE INVENTION

Plants of the new *Polemonium* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Golden Feathers'. These characteristics in combination distinguish 'Golden Feathers' as a new and distinct *Polemonium* plant:

1. Upright to somewhat outwardly spreading and mounding plant habit.
2. Dense and bushy appearance.
3. Green and yellow green variegated leaves.
4. Freely flowering habit.
5. Light purple-colored flowers.
6. Good garden performance.
7. Resistant to Powdery Mildew.

Plants of the new *Polemonium* and the mutation parent, 'Lambrook Mauve', differ primarily in leaf color as plants of 'Lambrook Mauve' have solid green-colored leaves whereas plants of the new *Polemonium* have green and yellow green variegated leaves.

Plants of the new *Polemonium* can be compared to plants of *Polemonium reptans* 'Stairway to Heaven', disclosed in U.S. Plant Pat. No. 15,187. In side-by-side comparisons, plants of the new *Polemonium* and 'Stairway to Heaven' differ primarily in the following characteristics:

1. Plants of the new *Polemonium* have green and yellow green variegated leaves whereas plants of 'Stairway to Heaven' have white and grey variegated leaves.
2. Plants of the new *Polemonium* have light purple-colored flowers whereas plants of 'Stairway to Heaven' have violet-colored flowers.

BRIEF DESCRIPTION OF THE PHOTOGRAPHS

The accompanying photographs illustrate the overall appearance of the new *Polemonium* plant showing the colors as true as it is reasonably possible to obtain in colored reproductions of this type. Colors in the photograph may differ slightly from the color values cited in the detailed botanical description which accurately describe the colors of the new *Polemonium* plant.

The photograph on the first sheet (FIG. 1) is a side perspective view of a typical plant of 'Golden Feathers' grown in a container.

Figure 2:
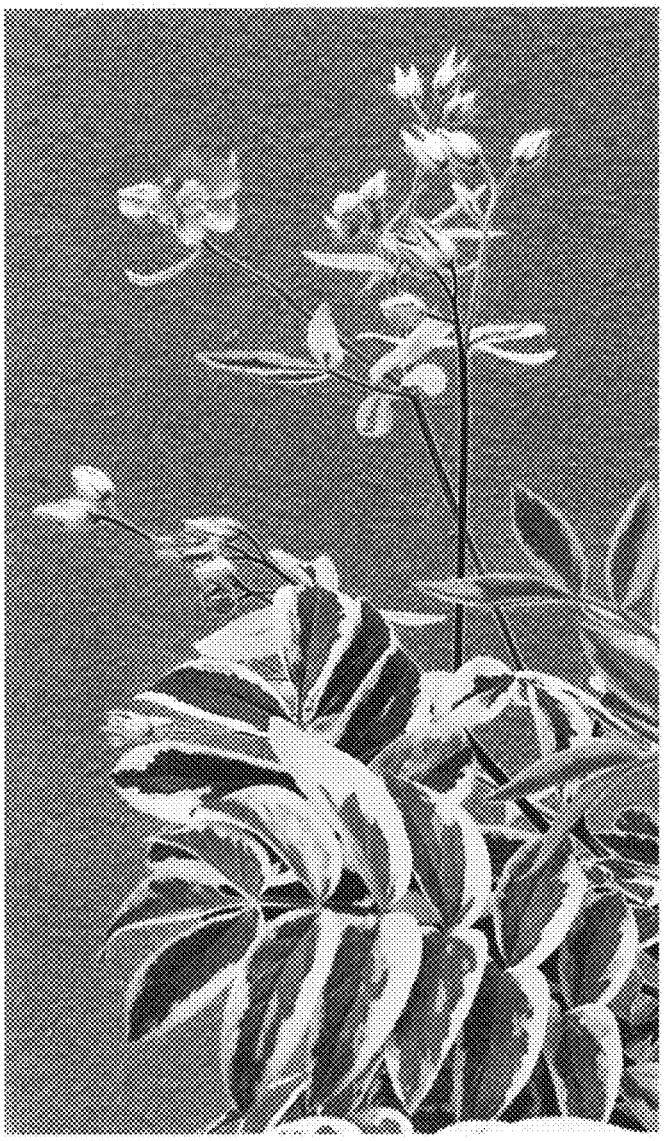

The photograph on the second sheet (FIG. 2) is a close-up view of a typical flowering plant of 'Golden Feathers'.

DETAILED BOTANICAL DESCRIPTION

The aforementioned photographs and following observations, measurements and values describe plants grown during the summer in an outdoor nursery in Fort Worth, Tex. and under cultural practices typical of commercial *Polemonium* production. During the production of the plants, day temperatures ranged from 35° C. to 40° C. and night temperatures ranged from 24° C. to 35° C. Plants were six months old when the photographs and the description were taken. In the description, color references are made to The Royal Horticultural Society Colour Chart, 2015 Edition, except where general terms of ordinary dictionary significance are used.

Botanical classification: *Polemonium pulcherrimum* 'Golden Feathers'.

Parentage: Naturally-occurring whole plant mutation of *Polemonium pulcherrimum* 'Lambrook Mauve', not patented.

*Type*.—By vegetative cuttings.

*Time to initiate roots, summer*.—About one to two weeks.

*Time to produce a rooted young plant, summer*.—About three weeks.

*Root description*.—Fine, fibrous; typically light brown in color, actual color of the roots is dependent on substrate composition, water quality, fertilizers, substrate temperature and physiological age of roots.

*Rooting habit*.—Freely branching; dense.

Plant description:

*Plant and growth habit*.—Herbaceous perennial; basal clumping habit; dense and bushy appearance; moderately vigorous growth habit.

*Plant height, soil level to copy of foliar plane*.—About 17 cm.

*Plant height, soil level to copy of floral plane*.—About 29 cm.

*Plant width (spread)*.—About 37.5 cm.

Leaf description:

*Arrangement*.—Simple or compound, oddly-pinnate, with about 15 to 17 leaflets per leaf; leaflets are sessile.

*Leaf length*.—About 12.5 cm.

*Leaf width*.—About 6 cm to 6.5 cm.

*Leaflet length*.—About 3 cm to 3.5 cm.

*Leaflet width*.—About 1.2 cm to 1.4 cm.

*Leaflet shape*.—Elliptical.

*Leaflet apex*.—Sharply acute.

*Leaflet base*.—Cuneate with oblique tendencies.

*Leaflet margin*.—Entire; not undulate.

*Leaflet texture and luster, upper and lower surfaces*.—Smooth, glabrous; matte.

*Leaflet venation pattern*.—Pinnate.

*Color*.—Developing leaves, upper surface: Variegated; centers, close to 146A, N137B and NN137B and towards the margins, close to 154C to 154D and N144C. Developing leaves, upper surface: Variegated; centers, close to 146A and 146B and towards the margins, close to N144C and N144D. Fully expanded leaves, upper surface: Variegated; centers, close to N137A to N137B and towards the margins, close to 8D, 11D and 154D with variable sectors, close to 148B and 148C; under low production temperatures, margins may be tinged with close to 187C to 187D. Fully expanded leaves, upper surface: Variegated; centers, close to 147B and towards the margins, close to 8D, 11D and 154D.

*Leaf petioles*.—Length: About 7.5 cm to 8.5 cm. Diameter: About 2.5 mm to 3 mm. Texture and luster, upper and lower surfaces: Smooth, glabrous; moderately glossy. Color, upper and lower surfaces: Close to 59A.

Flower description:

*Flower type and flowering habit*.—Single rotate flowers arranged in dichasial cymes; flowers face mostly outwardly; freely flowering habit with more than 100 flowers developing per plant during the flowering season.

*Fragrance*.—Very faintly fragrant.

*Natural flowering season*.—Long flowering period, plants flower continuously during the spring and summer.

*Flower longevity*.—Flowers last about one week on the plant; flowers not persistent.

*Flower buds*.—Height: About 5 mm. Diameter: About 3 mm. Shape: Ovoid. Texture and luster: Smooth, glabrous; matte. Color: Close to 8D.

*Inflorescence height*.—About 17 cm.

*Inflorescence diameter*.—About 10 cm.

*Flower diameter*.—About 1.25 cm.

*Flower depth*.—About 7.5 mm.

*Petals*.—Quantity per flower: Typically five in a single whorl. Length: About 6 mm. Width: About 6 mm. Shape: Spatulate. Apex: Rounded. Base: Cuneate. Margin: Entire; not undulate. Texture and luster, upper and lower surfaces: Smooth, glabrous; satiny; matte. Color: When opening, upper and lower surfaces: Close to 76A. Fully opened, upper and lower surfaces: Close to 76A; venation, close to 76A; color does not change with subsequent development.

*Sepals*.—Quantity per flower: Typically five in a single whorl, fused towards the base; calyx, campanulate. Length: About 8 mm. Width: About 2.5 mm. Shape: Free part, lanceolate. Apex: Acute. Margin: Entire; not undulate. Texture and luster, upper and lower surfaces: Smooth, glabrous; matte. Color: When opening, upper and lower surfaces: Close to 8D. Fully opened, upper and lower surfaces: Close to 8D.

*Peduncles*.—Length: About 10.5 cm. Diameter: About 2 mm. Strength: Strong, flexible. Texture and luster: Smooth, glabrous; matte. Color: Close to 137A variably tinged with close to 59A.

*Pedicels*.—Length: About 5 mm. Diameter: Less than 1 mm. Strength: Moderately strong, flexible. Texture and luster: Smooth, glabrous; matte. Color: Close to 146C.

*Reproductive organs*.—Stamens: Quantity per flower: Typically five. Filament length: About 3.5 mm to 4 mm. Filament color: Close to 16A. Anther size: About 2 mm by 1 mm. Anther shape: Oblong. Anther color: Close to 16A. Pollen amount: Scarce. Pollen color: Light orangish yellow. Pistils: Quantity per flower: One. Pistil length: About 4.5 mm. Stigma shape: Tubular. Stigma color: Close to 150D. Style length: About 3 mm. Style color: Close to 150D. Ovary color: Close to 150D.

*Fruits and seeds*.—To date, fruit and seed development has not been observed on plants of the new *Polemonium*.

Garden performance: Plants of the new *Polemonium* have been observed to have good garden performance and tolerate rain, wind, temperatures ranging from about 1° C. to about 40° C.

Pathogen & pest resistance: Plants of the new *Polemonium* have been observed to be resistent to Powdery Mildew (order *Erysiphales*). To date, plants of the new *Polemonium* have not been observed to be resistant to pests and other pathogens common to *Polemonium* plants.

It is claimed:

1. A new and distinct *Polemonium* plant named 'Golden Feathers' as illustrated and described.

* * * * *